United States Patent [19]

Schirmann et al.

[11] 3,948,902

[45] Apr. 6, 1976

[54] METHOD FOR PREPARING AZINES

[75] Inventors: Jean Pierre Schirmann, Brignais; Francis Weiss, Pierre-Benite, both of France

[73] Assignee: Produits Chimiques Ugine Kuhlmann, Paris, France

[22] Filed: Oct. 16, 1974

[21] Appl. No.: 515,156

Related U.S. Application Data

[63] Continuation of Ser. No. 267,921, June 30, 1972, abandoned.

[30] Foreign Application Priority Data

July 15, 1971 France............................. 71.25824

[52] U.S. Cl......................... 260/240 G; 260/566 B
[51] Int. Cl.$^2$..................................... C07C 109/00
[58] Field of Search..................... 260/566 B, 240 G

[56] References Cited
UNITED STATES PATENTS

2,870,206 1/1959 Meyer et al..................... 260/566 B
3,527,753 9/1970 Needham et al................ 260/566 B

*Primary Examiner*—Gerald A. Schwartz
*Attorney, Agent, or Firm*—Pennie & Edmonds

[57] ABSTRACT

A method is disclosed for preparing symmetrical azines of the formulas

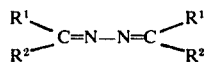 (I)

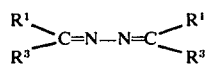

(II)

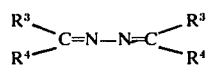

(III)

and unsymmetrical azines of the formulas

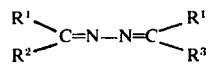 (IV)

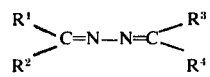

(V)

and mixtures of azines (I), (II) and (IV) and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing a benzene ring; further provided that $R^1$ and $R^2$ can be the same or different radicals, $R^3$ is a radical different from $R^1$ and $R^2$ and $R^3$ and $R^4$ are radicals different from each other and each is different from $R^1$ and $R^2$; or $R^1$ and $R^2$ or $R^1$ and $R^3$ or $R^3$ and $R^4$ bonded to the same carbon atom together form an unsubstituted or alkyl substituted alkylene radical of from 3 to 11 carbon atoms, each of the aforesaid radicals being unsubstituted or substituted with one or more radicals which are stable in the medium in which said azines are produced.

The method involves reacting in the liquid phase and in the absence of a nitrile, a carbonyl compound of the formula

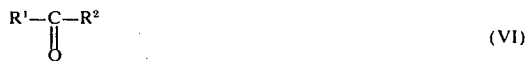 (VI)

alone or together with a different carbonyl compound

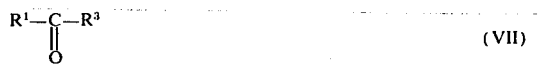 (VII)

or

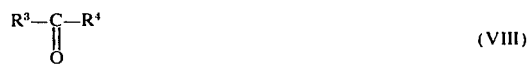 (VIII)

wherein $R^1$, $R^2$, $R^3$ and $R^4$ each has the same meaning defined above, with ammonia and hydrogen peroxide in the presence of an effective amount of at least one catalyst selected from the group consisting of the hydroxides and water soluble organic and inorganic salts of ammonium and the metals of Groups Ia and IIa of the Periodic Table of the Elements, and recovering the azine or mixture of azines from the reaction medium.

15 Claims, No Drawings

METHOD FOR PREPARING AZINES

This is a continuation of application Ser. No. 267,921, filed June 30, 1972, now abandoned.

BACKGROUND OF THE INVENTION

1. Field of the Invention

This invention relates to a method of preparing symmetrical azines as well as mixtures containing symmetrical and unsymmetrical azines.

2. Description of the Prior Art

Aldehydes are known to react with ammonia in a complex manner giving rise to various addition, condensation or polymerization products (see for example, *The Chemistry of the Carbon-Nitrogen Bond*, S. Patai, Interscience, London, 1967, page 67) which can react with hydrogen peroxide to form unstable peroxide products.

Moreover, it is known that ammonia, a ketone, and hydrogen peroxide react together to produce aminoperoxides (*J. Chem. Soc.* 1969, C, page 2663) and in the presence of such catalysts as tungstic or molybdic acid, a mixture of cyclohexanone and ammonia is oxidized by hydrogen peroxide to form cyclohexanoneoxime (*J. Gen. Chem.* (U.S.S.R.) 1960, 30, 1635).

Another method for preparing azines comprises the oxidation of ammonia in the presence of a ketone or aldehyde by means of an oxidizing medium comprising hydrogen peroxide and cyanogen or a nitrile. This method is fully disclosed in commonly assigned pending U.S. application Ser. No. 152,413, filed June 11, 1961, now abandoned.

Still another method for preparing azines comprises oxidizing a secondary alcohol in the liquid phase to form peroxide products of the auto-oxidation of the alcohol and subsequently reacting the peroxide products with ammonia in the presence of cyanogen or a nitrile. This method is fully disclosed in commonly assigned pending U.S. application Ser. No. 230,038, filed Feb. 28, 1972, now abandoned.

SUMMARY OF THE INVENTION

It has been surprisingly discovered that symmetrical azines of the formulas

  (I)

  (II)

  (III)

and unsymmetrical azines of the formulas

  (IV)

  (V)

can be conveniently prepared in good yields by reacting in the liquid phase and in the absence of a nitrile, a carbonyl compound of the formula

  (VI)

alone or together with a different carbonyl compound

  (VII)

or

  (VIII)

with ammonia and hydrogen peroxide in the presence of an effective amount of at least one catalyst selected from the group consisting of the hydroxides and water soluble organic and inorganic salts of ammonium and the metals of Groups Ia and IIa of the Periodic Table of the Elements, and recovering the azine or mixture of azines from the reaction medium.

$R^1$, $R^2$, $R^3$ and $R^4$ each has the same meaning defined above.

When a single carbonyl compound (VI) is reacted according to the method of this invention, a symmetrical azine having the formula

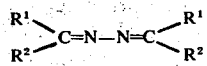  (I)

is produced.

When, for example, both $R^1$ and $R^2$ of carbonyl compound (VI) are hydrogen, the carbonyl compound is formaldehyde, and the azine resulting from this method is the symmetrical aldazine, formaldazine, which has the formula

When only one of the substituents is hydrogen, the resulting aldazine, has for example the formula

wherein the substituent $R^1$ is not hydrogen.

When neither of the substituents of the carbonyl compound (VI) is hydrogen, the carbonyl compound (VI) is a ketone and the resulting azine is a symmetrical ketazine of the formula

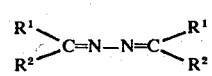  (I)

wherein none of the substituents $R^1$ and $R^2$ is hydrogen.

When in addition to carbonyl compound (VI), a different carbonyl compound (VII) is simultaneously reacted according to the method of this invention, a mixture of symmetrical and unsymmetrical azines of the formulas

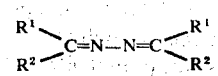  (I)

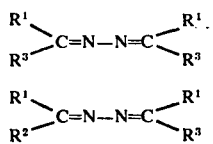

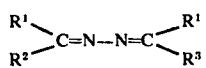

is produced.

And if in addition to carbonyl compound (VI), a different carbonyl compound (VIII) is simultaneously reacted according to the method of this invention, a mixture of symmetrical and unsymmetrical azines of the formulas

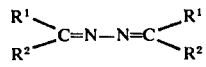

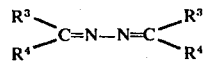

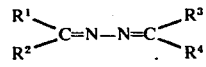

is produced.

When both carbonyl compounds (VI) and (VII) or (VI) and (VIII) are aldehydes, a mixture of symmetrical and unsymmetrical aldazines will be obtained. Similarly, if both carbonyl compounds (VI) and (VII) or (VI) and (VIII) are ketones, a mixture of symmetrical and unsymmetrical ketazines will be produced. And if one of the carbonyl compounds (VI), (VII) or (VIII) is an aldehyde and the other carbonyl compound which is being simultaneously reacted is a ketone, the method of this invention will yield a mixture of azines containing a symmetrical aldazine, a symmetrical ketazine and an unsymmetrical azine possessing the characteristics of both an aldazine and a ketazine.

Any number of different aldehydes and/or ketones may be reacted according to the method of this invention to yield mixtures of azines, the number of which are present in the mixture being made to depend upon the number of carbonyl compounds reacted.

The mechanism of the reaction taking place in the method of this invention remains unclear. Theoretically the overall reaction is considered to proceed as follows:

Some examples of ketones conforming to formula (VI), (VII) or (VIII) which are advantageously employed in the process of this invention include acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone and cyclododecanone.

The reaction of carbonyl compounds, ammonia and hydrogen peroxide is carried out in the liquid phase with a catalyst selected from the group consisting of the hydroxides and water soluble organic or inorganic salts of ammonium and the metals of Groups Ia and IIa of the Periodic Table of the Elements.

The salts of lithium, sodium, potassium, magnesium, calcium, strontium and barium have been found to be advantageous in carrying out the method of this invention.

The ammonium salts useful herein can be selected from amongst the derivatives of ammonia or the mono-, di- and tri-alkylamines in which the alkyl substituents contain from 1 to 12 carbon atoms. The hydroxides and quaternary ammonium salts can also be used, as, for example, the tetraalkylammonium hydroxides and salts in which the alkyl substituents contain from 1 to 12 carbon atoms or the benzyltrimethylammonium hydroxides and salts.

Salts which are useful in the method of this invention are, in the descending order of their solubility in the reaction medium, the salts of the mineral hydracids and oxyacids and the carboxylic and sulphonic aliphatic or aromatic acids containing not more than 20 carbon atoms whose anions are stable under the conditions of the reaction. Examples of such stable anions include the fluorides, chlorides, nitrates, sulfates, phosphates, pyrophosphates, borates, carbonates, formates, acetates, propionates, butyrates, isobutyrates, hexanoates, octanoates, dodecanoates, stearates, oxalates, succinates, glutarates, adipates, benzoates, phthalates, methanesulfonates, ethanesulfonates, benzenesulfonates and p-toluene sulfonates. The salts of numerous other anions can be employed herein as is readily recognized by one skilled in the art.

These salts can be added to the reaction medium

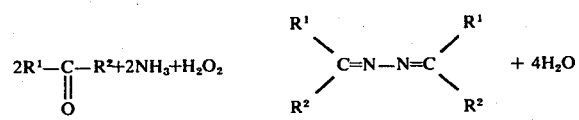

DETAILED DESCRIPTION OF THE INVENTION

The carbonyl compounds of this invention can contain substituents which are stable in the reaction medium such as chloro, bromo, fluoro, nitro and methoxy groups.

Some examples of aldehydes conforming to formulas (VI), (VII) or (VIII) which are advantageously employed in the process of this invention include formaldehyde, acetaldehyde, propionaldehyde, butyraldehyde, isobutyraldehyde, valeric aldehyde, pivalaldehyde, oenathal, 2-ethylhexanal, hexahydrobenzaldehyde, benzaldehyde, p-chlorobenzaldehyde, p-nitrobenzaldehyde and β-methoxypropionaldehyde.

preformed, however, when ammonium salts are employed, the latter can be prepared in situ by reacting ammonia which is a necessary reagent with the acid providing the desired anion.

The quantity of catalyst employed can vary over wide limits. Advantageously from about 0.01 to 10% by weight of the total weight of the reaction medium can be added as catalyst.

An advantageous method for preparing the azines according to this invention comprises reacting the three reagents, carbonyl compound, ammonia and hydrogen peroxide, as well as catalyst in aqueous solution or in the presence of a solvent which facilitates the homogenization of the mixture. This solvent is advantageously selected from among the alkyl monoalcohols having 1 to 4 carbon atoms, as, for example, methanol, ethanol, n-propanol, isopropanol, n-butanol, isobutanol and secondary butanol. Atmospheric pressure or a pressure of up to about 10 atmospheres can be used if such is necessary to maintain the ammonia in solution. Advantageously the temperature can vary from about 0° to 100°C.

The reactants can be employed in stoichiometric amounts but a molar lack or excess of one or several reagents can also be utilized. For example, from about 0.2 to about 5 moles of aldehyde or ketone or combined aldehyde(s) and/or ketone (s) and ammonia per mole of hydrogen peroxide can be employed and from about 2 to 4 moles of carbonyl compound and ammonia advantageously used. The reactants can be used in their commercially available form. For example, hydrogen peroxide can be used in aqueous solutions of 30–90% hydrogen peroxide by weight and ammonia can be used either in anhydrous form or in the usual aqueous solution.

The reactants can be introduced into the reactor either simultaneously or in random sequence at a rate which will permit effective control of the exothermic reaction. The carbonyl compounds of this invention can be reacted with hydrogen peroxide in the known manner and the resulting peroxides can then be reacted. Similarly, the carbonyl compounds of this invention can be reacted with ammonia before adding the hydrogen peroxide and catalyst. And finally, an aminoperoxide can be prepared in the known manner by the reaction of a carbonyl compound, ammonia and hydrogen peroxide and then introducing the catalyst into the reaction medium.

It is advantageous to add a stabilizing agent for hydrogen peroxide to the reaction medium such as phosphoric acid, nitrilotriacetic acid, ethylenediaminetetraacetic acid or the sodium salts of the aforesaid acids.

Azines are very useful as intermediate products for a variety of syntheses, particularly in the manufacture of hydrazine and numerous organic nitrogen compounds employed as pesticides or as pharmaceutical products. In the manufacture of hydrazine, for example, azines can be reacted with water and/or a strong acid to produce hydrazine hydrate and/or a hydrazine salt. The hydrazine hydrate and/or hydrazine salt are readily converted to hydrazine employing well known processes.

Examples 1 through 6 demonstrate the process of this invention for the production of a symmetrical aldazine and ketazines conforming to formula (I). By utilizing the same procedures as disclosed in the Examples except that two or more different aldehydes or ketones or one or more aldehyde and ketone is reacted, a mixture of symmetrical and unsymmetrical azines will result as hereinbefore described.

EXAMPLE I

A solution of 20 gm. of sodium hydroxide, 200 gm. of methanol and 10 cm$^3$ of water were placed in a glass reactor equipped with a mechanical agitator. 73.5 gm. of cyclohexanone, 25 cm$^3$ of 19% solution of ammonia and 0.5 gm. of the disodium salt of ethylenediaminetetraacetic acid were then added to the solution. Thereafter over a period of 30 minutes while maintaining a temperature of 20°C., 12.25 gm. of 70% hydrogen peroxide were added. After 24 hours, the reaction medium contained 8.6 gm. of cyclohexanoneazine.

EXAMPLE II

EXAMPLE I was substantially repeated replacing sodium hydroxide with an equal amount of lithium chloride. After the hydrogen peroxide was added, the reaction medium was heated for 2 hours at 50°C. after which the medium contained 15.4 gm. of cyclohexanoneazine.

EXAMPLE III

The method reported in *J. Chem. Soc.*, 1969, c. p. 2678 was used for preparing peroxy-1,1'-dicyclohexylamine.

98 gm. of cyclohexanone, 20 cm$^3$ water, 45 cm$^3$ of methanol, 50 cm$^3$ of a 19% solution of ammonia and 1 gm. of the disodium salt of ethylenediaminetetraacetic acid were mixed together. Gaseous ammonia was bubbled into the reaction medium, the medium was cooled to 0°C and 24.5 gm. of a 70% solution of hydrogen peroxide were then progressively added to the medium. The medium was left at ambient temperature for 24 hours after which 101 gm. of peroxy-1,1-dicyclohexylamine were measured therein.

A portion of the medium containing 53 gm. of peroxy-1,1'-dicyclohexylamine was combined with 24.5 gm. of cyclohexanone and 20 gm. of sodium hydroxide previously dissolved in 100 cm$^3$ methanol. The temperature of the mixture was raised to 50°C. for 6½ hours. The mixture was maintained saturated with ammonia by bubbling the reagent therein. 2.3 gm. cyclohexanoneazine were measured in the mixture at the end of the reaction period.

EXAMPLE IV 42 gm. of peroxy-1,1'-dicyclohexylamine prepared as in EXAMPLE 3, 20 gm. cyclohexanone (0.22 moles), 10 gm. of lithium chloride and 100 cm$^3$ of methanol were mixed together. This mixture was saturated with ammonia bubbled therein and the temperature of the mixture was increased to 35°C. After 6 hours of reaction time, the mixture contained 3.1 gm. of cyclohexanoneazine.

EXAMPLE V

Peroxy-1,1'-diisopropylamine was prepared according to the method described in the literature and mixed at 0°C. with 58 gm. of acetone in 70 cm$^3$ of a 30% weight solution of hydrogen peroxide in the presence of previously bubbled-in ammonia, 1 gm. of the disodium salt of ethylenediaminetetraacetic acid and 1 gm. of ammonium acetate. The temperature of the mixture was increased to 0°C. for 24 hours.

A portion of the mixture containing 13.1 gm. of peroxy-1,1'-diisopropylamine was dissolved in 50 cm$^3$ methanol, 5.8 gm. of acetone and 20 gm. of lithium bromide were added, ammonia was bubbled in and the temperature of the mixture was increased to 35°C. After reacting for two hours, the mixture contained 0.22 gm. of acetoneazine.

EXAMPLE VI 20 gm. of peroxy-1,1'-diisobutylaminen were prepared according to the method described in *J. Chem. Soc.* 1969, 6, page 2678, by the reaction of hydrogen peroxide with isobutyraldehyde in the presence of ammonia. 7 gm. of isobutyraldehyde and 10 gm. of lithium chloride were added to the crude reaction mixture and thereafter the mixture was saturated with ammonia being bubbled therein. The temperature of the reaction mixture was increased to 35°C. and after 6 hours, the mixture contained 1.4 gm. of isobutyraldehydeazine.

We claim:

1. A method for preparing symmetrical azines of the formulas

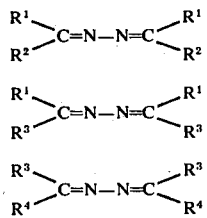

and unsymmetrical azines of the formulas

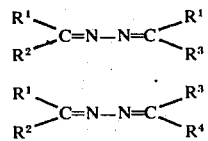

and mixtures of azines (I), (II), and (IV), and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, or a phenyl radical; further provided that $R^1$ and $R^2$ can be the same or different radicals, $R^3$ is a radical different from $R^1$ and $R^2$ and $R^3$ and $R^4$ are radicals different from each other and each is different from $R^1$ and $R^2$; or $R^1$ and $R^2$ or $R^1$ and $R^3$ or $R^3$ and $R^4$ bonded to the same carbon atom together from an unsubstituted or alkyl substituted alkylene radical of from 3 to 11 carbon atoms, each of the aforesaid radicals being unsubstituted or substituted with one or more chlorine or fluorine atoms or nitro or methoxy groups, which comprises reacting in the absence of a nitrile and in the liquid phase a carbonyl compound of the formula

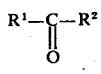

alone or together with a different carbonyl compound

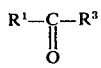

or

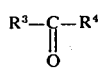

wherein $R^1$, $R^2$, $R^3$ and $R^4$ each has the same meaning as defined above, with ammonia and hydrogen peroxide in the presence of an effective amount of at least one catalyst selected from the hydroxides and chloride, fluoride, nitrate, sulfate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulfonate, ethanesulfonate, benzenesulfonate, and p-toluene sulfonate salts of the metals of Groups Ia and IIa of the Periodic Table of the Elements, ammonia, mono-, di-, and trialkylamines wherein the alkyl substituents have from 1 to 12 carbon atoms, tetraalkylammonium wherein the alkyl substituents have from 1 to 12 carbon atoms, and benzyltrimethylammonium, and recovering the azine or mixtures of azines from the reaction medium.

2. The method of claim 1 wherein the cationic portion of the salts is lithium, sodium, potassium, magnesium, calcium, strontium or barium.

3. A method for preparing azines which comprises reacting in the absence of a nitrile and in the liquid phase ammonia, hydrogen peroxide, and a carbonyl compound selected from formaldehyde, acetaldehyde, propionaldehyde, butyraldehyde, isobutyraldehyde, valerylaldehyde, pivalaldehyde, oenanthal, 2-ethylhexanal, hexahydrobenzaldehyde, benzaldehyde, p-chlorobenzaldehyde, p-nitrobenzaldehyde, β-methoxypropionaldehyde 2-butanone, 2-pentanone, 3-pentanone, methylisopropylketone, methylisobutylketone, methcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone, and cyclododecanone, and mixtures thereof, in the presence of an effective amount of a catalyst selected from the hydroxides and the chloride, fluoride, nitrate, sulfate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulfonate, ethanesulfonate, benzene sulfonate, and p-toluene sulfonate salts of the metals of Groups Ia and IIa of the Periodic Table of the Elements, ammonia, mono-, di-, and trialkylamines wherein the alkyl substituents have from 1 to 12 carbon atoms, tetraalkylammonium wherein the alkyl substituents have from 1 to 12 carbon atoms, and benzyltrimethylammonium, and recovering the azine or mixtures of azines from the reaction medium.

4. The method of claim 1 wherein one aldehyde conforming to the formula of carbonyl compound (VI) is reacted.

5. The method of claim 4 wherein the aldehyde is formaldehyde, acetaldehyde, proprionaldehyde, butyraldehyde, isobutyraldehyde, valerylaldehyde, pivaldehyde, oenanthal, 2-ethylhexanol, hexahydrobenzaldehyde, benzaldehyde, p-chlorobenzaldehyde, p-nitrobenzaldehyde, or β-methoxyproprionaldehyde.

6. The method of claim 1 wherein one ketone conforming to the formula of carbonyl compound (VI) is reacted.

7. The method of claim 6 wherein the ketone is acetone, 2-butanone, 2-pentanone, 3-pentanone, methylisopropylketone, methylisobutylketone, methycyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone or cyclododecanone.

8. The method of claim 1 wherein the carbonyl compound (VI) is reacted together with the different carbonyl compound (VII) or (VIII).

9. The method of claim 8 wherein both carbonyl compounds (VI) and (VII) or (VI) and (VIII) are aldehydes.

10. The method of claim 8 wherein both carbonyl compounds (VI) and (VII) or (VI) and (VIII) are ketones.

11. The method of claim 8 wherein the carbonyl compound (VI) is an aldehyde and the carbonyl compound (VII) or (VIII) is a ketone.

12. The method of claim 1 wherein the reaction takes place in the presence of a solvent.

13. The method of claim 12 wherein the solvent employed is an alkyl monoalcohol or from 1 to 4 carbon atoms.

14. The method of claim 1 wherein the reaction is carried out at a temperature between about 0° and 100°C.

15. The method of claim 1 wherein the molar ratios of carbonyl compound and ammonia to hydrogen peroxide is between about 2:1 and 4:1.

* * * * *

UNITED STATES PATENT AND TRADEMARK OFFICE
CERTIFICATE OF CORRECTION

PATENT NO. : 3,948,902
DATED : April 6, 1976
INVENTOR(S) : JEAN-PIERRE SCHIRMANN ET AL.

It is certified that error appears in the above-identified patent and that said Letters Patent are hereby corrected as shown below:

Column 1, line 33, "1961" should read -- 1971 --;

line 37, "peroxide" should read -- peroxidic --.

Column 3, line 19, "(I)" should read -- (III) --;

line 22, "(IV)" should read -- (V) --;

line 51, "+H$_2$O$_2$" should read -- +H$_2$O$_2 \rightarrow$ --.

Column 5, line 49, "1 through 6" should read -- I through VI --.

Column 6, line 62, "peroxy-1,1'-diisobutylaminen" should read -- peroxy-1,1'-diisobutylamine --.

Column 8, lines 51-52, "pivaldehyde" should read -- pivalaldehyde --.

Column 10, line 4, "or from" should read -- of from --

Signed and Sealed this

Twentieth Day of July 1976

[SEAL]

Attest:

RUTH C. MASON
*Attesting Officer*

C. MARSHALL DANN
*Commissioner of Patents and Trademarks*